United States Patent
Marinescu et al.

(10) Patent No.: US 11,705,247 B2
(45) Date of Patent: Jul. 18, 2023

(54) PREDICTIVE CONTACT TRACING

(71) Applicant: International Business Machines Corporation, Armonk, NY (US)

(72) Inventors: Radu Marinescu, Dublin (IE); Akihiro Kishimoto, Setagaya (JP)

(73) Assignee: International Business Machines Corporation, Armonk, NY (US)

( * ) Notice: Subject to any disclaimer, the term of this patent is extended or adjusted under 35 U.S.C. 154(b) by 244 days.

(21) Appl. No.: 16/952,219

(22) Filed: Nov. 19, 2020

(65) Prior Publication Data
US 2022/0157473 A1     May 19, 2022

(51) Int. Cl.
*G16H 50/80* (2018.01)
*G06F 17/18* (2006.01)
(Continued)

(52) U.S. Cl.
CPC ......... *G16H 50/80* (2018.01); *G06F 16/9024* (2019.01); *G06F 17/18* (2013.01); *G16H 15/00* (2018.01)

(58) Field of Classification Search
CPC .... G16H 15/00; G16H 50/80; G06F 16/9024; G06F 17/18
See application file for complete search history.

(56) References Cited

U.S. PATENT DOCUMENTS 8,560,339 B2 * 10/2013 Khan .................. G06Q 10/04
                                                    705/2
10,251,610 B2    4/2019 Parthasarathy
(Continued)

FOREIGN PATENT DOCUMENTS

CA        3027424 A1 *  1/2018  ............... G06F 7/00
CN      110223785 A  *  9/2019
(Continued)

OTHER PUBLICATIONS

Park, Ok, et al. "Contact transmission of Covid-19 in South Korea: Novel investigation techniques fortracing contacts." Osong Public Health and Research Perspectives 1 (May 2020). (Year: 2020).*
(Continued)

*Primary Examiner* — Mamon Obeid
*Assistant Examiner* — Chance L Smith
(74) *Attorney, Agent, or Firm* — Michael O'Keefe

(57) ABSTRACT

In an approach to predictive contact tracing, a computer receives a query associated with contact tracing of a person with an infection. A computer retrieves timestamped location data associated with the person over a period of time. Based on the retrieved data, a computer creates a contact graph associated with the person, where the contact graph depicts one or more other people that were in contact with the person over the period of time. A computer retrieves medical data associated with the person and the one or more other people that were in contact with the person over the period of time. Based on the retrieved data, a computer builds a probabilistic model. A computer runs the probabilistic model to provide a prediction of a probability of infection of the one or more other people over the period of time as a result of being in contact with the person.

20 Claims, 4 Drawing Sheets

(51) Int. Cl.
*G06F 16/901* (2019.01)
*G16H 15/00* (2018.01)

(56) References Cited

U.S. PATENT DOCUMENTS

| | | | | |
|---|---|---|---|---|
| 2011/0093249 | A1* | 4/2011 | Holmes | G16H 50/80 |
| | | | | 703/6 |
| 2013/0031179 | A1* | 1/2013 | Christakis | G16H 50/80 |
| | | | | 709/204 |
| 2017/0024531 | A1* | 1/2017 | Malaviya | G16H 50/30 |
| 2018/0052970 | A1* | 2/2018 | Boss | G06F 21/35 |
| 2019/0138691 | A1* | 5/2019 | Hu | G06N 20/00 |
| 2021/0050116 | A1* | 2/2021 | Sabeti | G16H 50/50 |
| 2022/0030382 | A1* | 1/2022 | Klasson | G16H 50/20 |
| 2022/0037032 | A1* | 2/2022 | Subramanian | G06F 16/90332 |

FOREIGN PATENT DOCUMENTS

| | | | |
|---|---|---|---|
| CN | 111126535 A | | 5/2020 |
| CN | 111739657 B | * | 12/2020 |
| JP | 2011065540 A | | 3/2011 |

OTHER PUBLICATIONS

Colubri, Andres, et al. "Individual-level modeling of COVID-19 epidemic risk." arXiv preprint arXiv:2006.16761 (Aug. 2020). (Year: 2020).*

Dong, Wen, Katherine Heller, and Alex Sandy Pentland. "Modeling infection with multi-agent dynamics." International Conference on Social Computing, Behavioral-Cultural Modeling, and Prediction. Springer, Berlin, Heidelberg, 2012. (Year: 2012).*

Dong, Wen, Alex Pentland, and Katherine A. Heller. "Graph-coupled HMMs for modeling the spread of infection." arXiv preprint arXiv:1210.4864 (2012). (Year: 2012).*

Dong, Wen, et al. "PocketCare: Tracking the flu with mobile phones using partial observations of proximity and symptoms." Proceedings of the ACM on Interactive, Mobile, Wearable and Ubiquitous Technologies 3.2 (2019): 1-23. (Year: 2019).*

Baker, A., et al. "Epidemic mitigation by statistical inference from contact tracing data." (Sep. 2020). (Year: 2020).*

Bengio, Yoshua, et al. "Predicting infectiousness for proactive contact tracing." arXiv preprint arXiv:2010.12536 (Oct. 2020). (Year: 2020).*

Briers, Mark, Marcos Charalambides, and Chris Holmes. "Risk scoring calculation for the current NHSx contact tracing app." arXiv preprint arXiv:2005.11057 (May 2020). (Year: 2020).*

Lauer, Stephen A., Alexandria C. Brown, and Nicholas G. Reich. "Infectious Disease Forecasting for." Population biology of vector-borne diseases (May 2020): 45. (Year: 2020).*

Leung, Abby, et al. "Contact graph epidemic modelling of covid-19 for transmission and intervention strategies." arXiv preprint arXiv:2010.03081 (Oct. 2020). (Year: 2020).*

Liu, Shangching, et al. "Continuous Learning and Inference of Individual Probability of SARS-CoV-2 Infection Based on Interaction Data." arXiv preprint arXiv:2006.04646 (Jun. 2020). (Year: 2020).*

Zhou, Chuansai, et al. "Detecting suspected epidemic cases using trajectory big data." arXiv preprint arXiv:2004.00908 (Apr. 2020). (Year: 2020).*

Anonymous et al., "Apple and Google partner on COVID-19 contact tracing technology", Apple Inc. Newsroom, United States, Apr. 10, 2020, 3 Pages.

Authors et al. Disclosed Anonymously, "Location-Free Tracing and Notification of Infected Individuals", An IP.com Prior Art Database Technical Disclosure, IP.com No. IPCOM000262482D, Jun. 4, 2020, 3 Pages.

Authors et al. Disclosed Anonymously, "System and method for a community of users to detect and control the propagation of contagious disease using a novel contact tracing algorithm", An IP.com Prior Art Database Technical Disclosure, IP.com No. IPCOM000262367D, May 24, 2020, 6 Pages.

Bay et al., "BlueTrace: A privacy-preserving protocol for community-driven contact tracing across borders", BlueTrace Protocol, Apr. 9, 2020, 9 Pages.

* cited by examiner

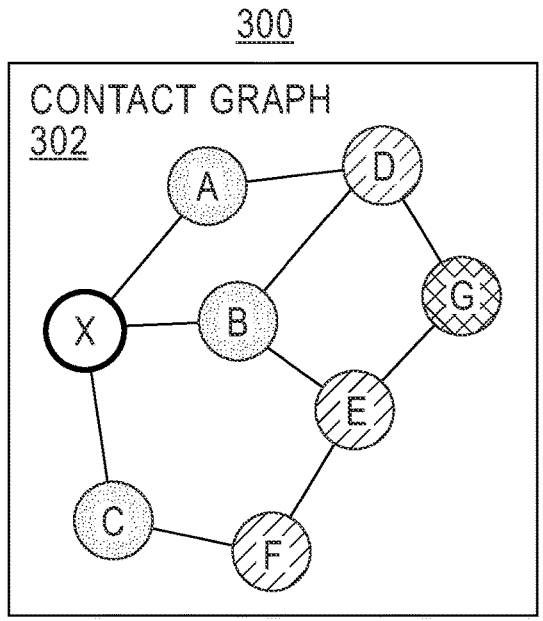
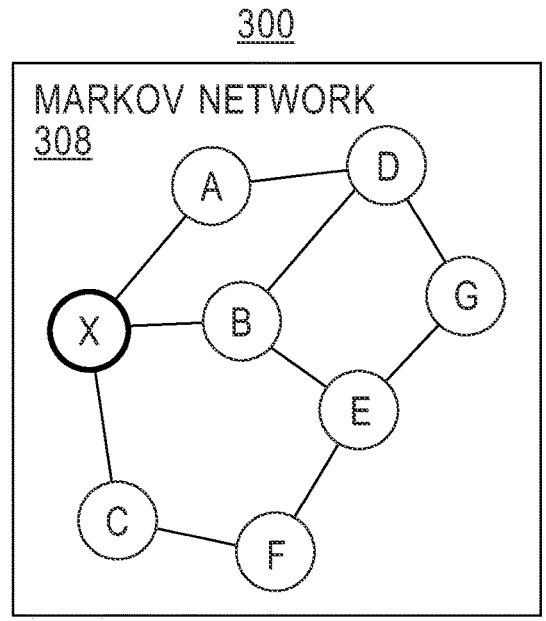
FIG. 3A
FIG. 3C
| TIME | X | A | B | C | D | E | F | G |
|---|---|---|---|---|---|---|---|---|
| 1 | Y | N |   | N | N |   | N | N |
| 2 | Y | N |   | N | N |   | N | Y |
| 3 | Y | N | N | N | Y |   | Y | Y |
| 4 | Y | N | N | Y | Y |   | Y | Y |
| ... |   |   |   |   |   |   |   |   |
KEY:
Y - INFECTED
N - NOT INFECTED
FIG. 3B

PREDICTIVE CONTACT TRACING

BACKGROUND OF THE INVENTION

The present invention relates generally to the field of probabilistic modeling, and more particularly to predictive contact tracing.

Contact tracing is an important tool for reducing the spread of infectious diseases. The goal of contact tracing is to reduce an effective reproductive number (R) of the disease by identifying people who have been exposed to a virus through an infected person and contacting them to provide early detection, tailored guidance, and timely treatment. By stopping virus transmission chains, contact tracing helps "flatten the curve" and reduces the peak burden of a disease on a healthcare system.

Predictive modeling uses statistics to predict outcomes. Most often an event one wants to predict is in the future, but predictive modeling can be applied to any type of unknown event, regardless of when the event occurred. Probabilistic forecasting summarizes what is known about, or opinions about, future events. In contrast to single-valued forecasts (such as forecasting that the maximum temperature at a given site on a given day will be 73 degrees Fahrenheit, or that the result in a given football game will be a tie), probabilistic forecasts assign a probability to each of a number of different outcomes, and the complete set of probabilities represents a probability forecast. A Markov network is a graphical model used in probabilistic forecasting that depicts dependencies between different entities.

SUMMARY

Embodiments of the present invention disclose a computer-implemented method, a computer program product, and a system for predictive contact tracing. The computer-implemented method may include one or more computer processors receiving a query associated with contact tracing of a person with an infection. One or more computer processors retrieve timestamped location data associated with the person over a period of time. Based on the retrieved timestamped location data, one or more computer processors create a contact graph associated with the person, where the contact graph depicts one or more other people that were in contact with the person over the period of time. One or more computer processors retrieve medical data associated with the person and the one or more other people that were in contact with the person over the period of time. Based on the retrieved timestamped location data and on the retrieved medical data, one or more computer processors build a probabilistic model. One or more computer processors run the probabilistic model to provide a prediction of a probability of infection of the one or more other people over the period of time as a result of being in contact with the person.

BRIEF DESCRIPTION OF THE DRAWINGS

FIG. 3A illustrates an example of a contact graph created by the contact tracing engine, on the server computer within the distributed data processing environment of FIG. 1, in accordance with an embodiment of the present invention;

FIG. 3B illustrates an example of tabulated medical data used by the contact tracing engine to build a Markov network model, on the server computer within the distributed data processing environment of FIG. 1, in accordance with an embodiment of the present invention;

FIG. 3C illustrates an example of the Markov network model built by the contact tracing engine, on the server computer within the distributed data processing environment of FIG. 1, in accordance with an embodiment of the present invention.

DETAILED DESCRIPTION

During a pandemic, determining a list of people that an already-infected person could potentially infect with the virus is called contact tracing. Accurate contact tracing for infected individuals is crucial for the authorities to be able to slow down the spread of the infection. This is especially important when the pathogen has a high reproduction rate, for example, $R_0 > 4$. In this case, thousands of people could be infected over a short period of time by just one single individual. Public safety during a pandemic is paramount as massive loss of human life could be devastating and have long lasting social and economic impacts. Contact tracing is typically done manually. For example, a local health department manually checks the potential cluster of infections by following up with the people with whom an infected person might have been in contact. The process is prone to errors, as it is dependent, at least in part, on the memory of the infected person, and therefore can be highly inaccurate.

Embodiments of the present invention recognize that efficiency may be gained by automating contact tracing using available data. Embodiments of the present invention also recognize that controlling the spread of infection can be facilitated by accurate and effective contact tracing, enabling early detection of a cluster of potentially infected people. Embodiments of the present invention also recognize that contact tracing can be improved by providing a prediction of likely infection in the future. Implementation of embodiments of the invention may take a variety of forms, and exemplary implementation details are discussed subsequently with reference to the Figures.

Figure 1:
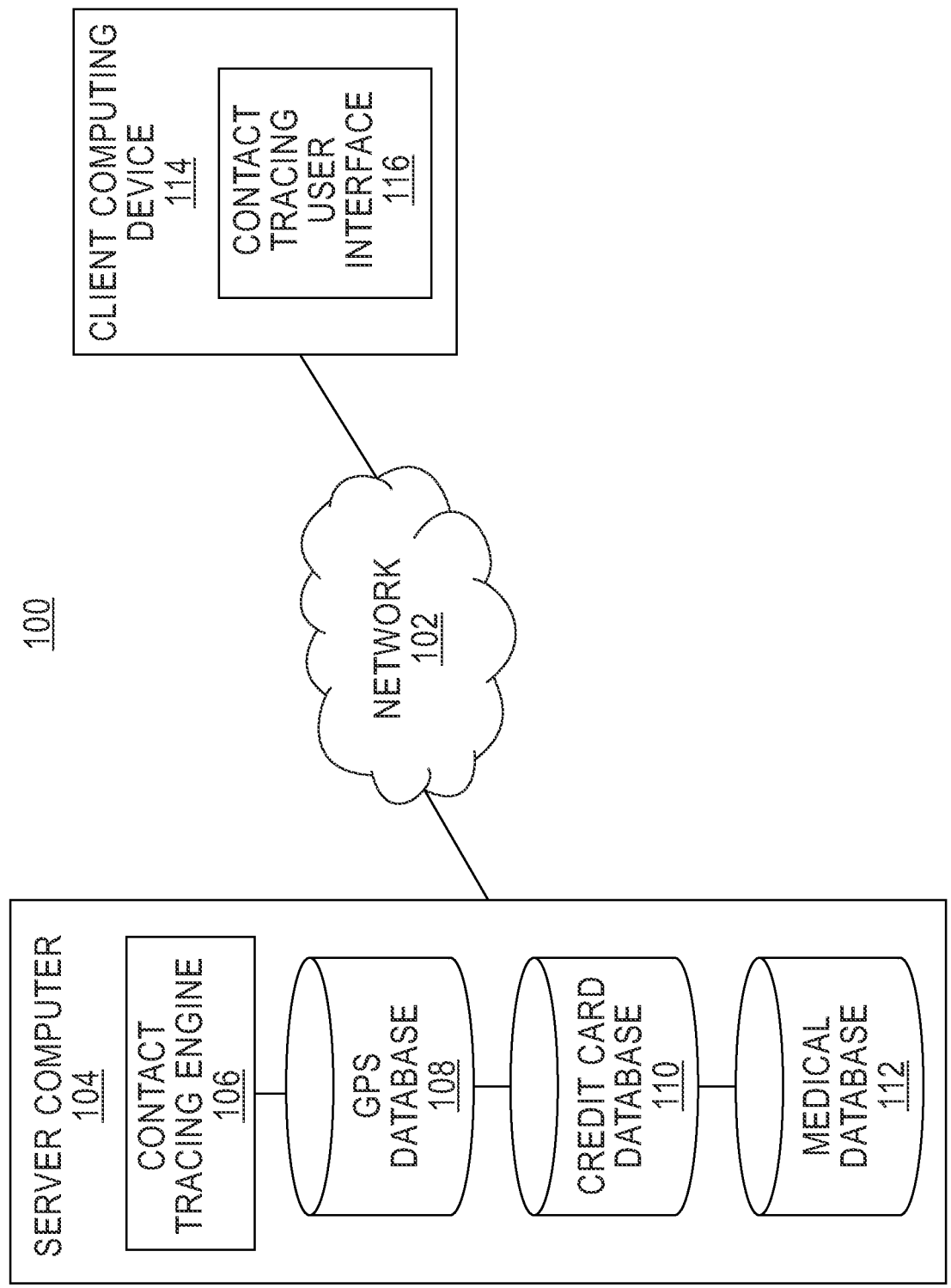
FIG. 1 is a functional block diagram illustrating a distributed data processing environment, in accordance with an embodiment of the present invention.

FIG. 1 is a functional block diagram illustrating a distributed data processing environment, generally designated 100, in accordance with one embodiment of the present invention. The term "distributed" as used herein describes a computer system that includes multiple, physically distinct devices that operate together as a single computer system. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims.

Distributed data processing environment 100 includes server computer 104 and client computing device 114, interconnected over network 102. Network 102 can be, for example, a telecommunications network, a local area network (LAN), a wide area network (WAN), such as the Internet, or a combination of the three, and can include wired, wireless, or fiber optic connections. Network 102 can include one or more wired and/or wireless networks capable of receiving and transmitting data, voice, and/or video signals, including multimedia signals that include voice, data, and video information. In general, network 102 can be any combination of connections and protocols that will support communications between server computer 104, client computing device 114, and other computing devices (not shown) within distributed data processing environment 100.

Server computer 104 can be a standalone computing device, a management server, a web server, a mobile computing device, or any other electronic device or computing system capable of receiving, sending, and processing data. In other embodiments, server computer 104 can represent a server computing system utilizing multiple computers as a server system, such as in a cloud computing environment. In another embodiment, server computer 104 can be a laptop computer, a tablet computer, a netbook computer, a personal computer (PC), a desktop computer, a personal digital assistant (PDA), a smart phone, or any programmable electronic device capable of communicating with client computing device 114 and other computing devices (not shown) within distributed data processing environment 100 via network 102. In another embodiment, server computer 104 represents a computing system utilizing clustered computers and components (e.g., database server computers, application server computers, etc.) that act as a single pool of seamless resources when accessed within distributed data processing environment 100. Server computer 104 includes contact tracing engine 106, global positioning system (GPS) database 108, credit card database 110, and medical database 112. Server computer 104 may include internal and external hardware components, as depicted and described in further detail with respect to FIG. 4.

Contact tracing engine 106 uses available data to build a probabilistic model to predict a likelihood that a person in contact with an infected person could have been infected over a period of time in the past, and then uses the probabilistic model to build a dynamic probabilistic model that predicts a likelihood of a contact being infected at a time in the future. Contact tracing engine 106 receives a query associated with contact tracing of a group of people from a user. Contact tracing engine 106 retrieves timestamped location data associated with the group of people. Contact tracing engine 106 creates a contact graph based on the timestamped location data. Contact tracing engine 106 builds and runs a Markov network. Contact tracing engine 106 determines if the query included a future time horizon, and, if so, then contact tracing engine 106 uses the Markov network to build and run a dynamic probabilistic model. Contact tracing engine 106 generates a report based on the modeling data and transmits the report to the user. Contact tracing engine 106 is depicted and described in further detail with respect to FIG. 2 and FIGS. 3A, 3B, and 3C.

GPS database 108, credit card database 110, and medical database 112 are each a repository for data used by contact tracing engine 106. In the depicted embodiment, GPS database 108, credit card database 110, and medical database 112 reside on server computer 104. In another embodiment, GPS database 108, credit card database 110, and medical database 112 may each reside elsewhere within distributed data processing environment 100, provided contact tracing engine 106 has access to GPS database 108, credit card database 110, and medical database 112. In the depicted embodiment, GPS database 108, credit card database 110, and medical database 112 are each a separate database. In another embodiment, GPS database 108, credit card database 110, and medical database 112 may be combined into a single database. In a further embodiment, GPS database 108, credit card database 110, and medical database 112 may be combined into any combination of one or more databases. A database is an organized collection of data. GPS database 108, credit card database 110, and medical database 112 can each be implemented with any type of storage device capable of storing data and configuration files that can be accessed and utilized by contact tracing engine 106, such as a database server, a hard disk drive, or a flash memory. GPS database 108 stores location data collected over time associated with one or more users of devices enabled with GPS tracking, such as a user of client computing device 114. Credit card database 110 stores credit card transaction data associated with one or more users. Credit card transaction data includes, but is not limited to, credit card company name, credit card user name, credit card number, credit card expiration date, credit card verification number, timestamp of credit card transaction, location of credit card transaction, and amount of credit card transaction. Medical database 112 stores medical information and data associated with one or more users. Medical information and data include, but are not limited to, a user name, a user address, a user phone number, a medical condition of a user, and one or more test results of a user.

The present invention may contain various accessible data sources, such as GPS database 108, credit card database 110, and medical database 112, that may include personal data, content, or information the user wishes not to be processed. Personal data includes personally identifying information or sensitive personal information as well as user information, such as tracking or geolocation information. Processing refers to any operation, automated or unautomated, or set of operations such as collecting, recording, organizing, structuring, storing, adapting, altering, retrieving, consulting, using, disclosing by transmission, dissemination, or otherwise making available, combining, restricting, erasing, or destroying personal data. Contact tracing engine 106 enables the authorized and secure processing of personal data. Contact tracing engine 106 provides informed consent, with notice of the collection of personal data, allowing the user to opt in or opt out of processing personal data. Consent can take several forms. Opt-in consent can impose on the user to take an affirmative action before personal data is processed. Alternatively, opt-out consent can impose on the user to take an affirmative action to prevent the processing of personal data before personal data is processed. Contact tracing engine 106 provides information regarding personal data and the nature (e.g., type, scope, purpose, duration, etc.) of the processing. Contact tracing engine 106 provides the user with copies of stored personal data. Contact tracing engine 106 allows the correction or completion of incorrect or incomplete personal data. Contact tracing engine 106 allows the immediate deletion of personal data.

Client computing device 114 can be one or more of a laptop computer, a tablet computer, a smart phone, a smart watch, a smart speaker, or any programmable electronic device capable of communicating with various components and devices within distributed data processing environment 100, via network 102. Client computing device 114 may be a wearable computer. Wearable computers are miniature electronic devices that may be worn by the bearer under, with, or on top of clothing, as well as in or connected to glasses, hats, or other accessories. Wearable computers are especially useful for applications that require more complex computational support than merely hardware coded logics. In one embodiment, the wearable computer may be in the form of a head mounted display. The head mounted display may take the form-factor of a pair of glasses. In an embodiment, the wearable computer may be in the form of a smart watch or a smart tattoo. In an embodiment, client computing device 114 may be integrated into a vehicle of the user. For example, client computing device 114 may include a heads-up display in the windshield of the vehicle. In general, client computing device 114 each represents one or more programmable electronic devices or combination of programmable electronic devices capable of executing machine readable program instructions and communicating with other computing devices (not shown) within distributed data processing environment 100 via a network, such as network 102. Client computing device 114 includes an instance of contact tracing user interface 116.

Contact tracing user interface 116 provides an interface between contact tracing engine 106 on server computer 104 and a user of client computing device 114. In one embodiment, contact tracing user interface 116 is mobile application software. Mobile application software, or an "app," is a computer program designed to run on smart phones, tablet computers and other mobile devices. In one embodiment, contact tracing user interface 116 may be a graphical user interface (GUI) or a web user interface (WUI) and can display text, documents, web browser windows, user options, application interfaces, and instructions for operation, and include the information (such as graphic, text, and sound) that a program presents to a user and the control sequences the user employs to control the program. Contact tracing user interface 116 enables a user of client computing device 114 to interact with contact tracing engine 106. For example, contact tracing user interface 116 enables a user of client computing device 114 to query contact tracing engine 106 for contact tracing information. In another example, contact tracing user interface 116 may enable a user of client computing device 114 to opt in to contact tracing engine 106. In an embodiment, contact tracing user interface 116 enables a user to submit data to one or more of GPS database 108, credit card database 110, and medical database 112.

Figure 2:
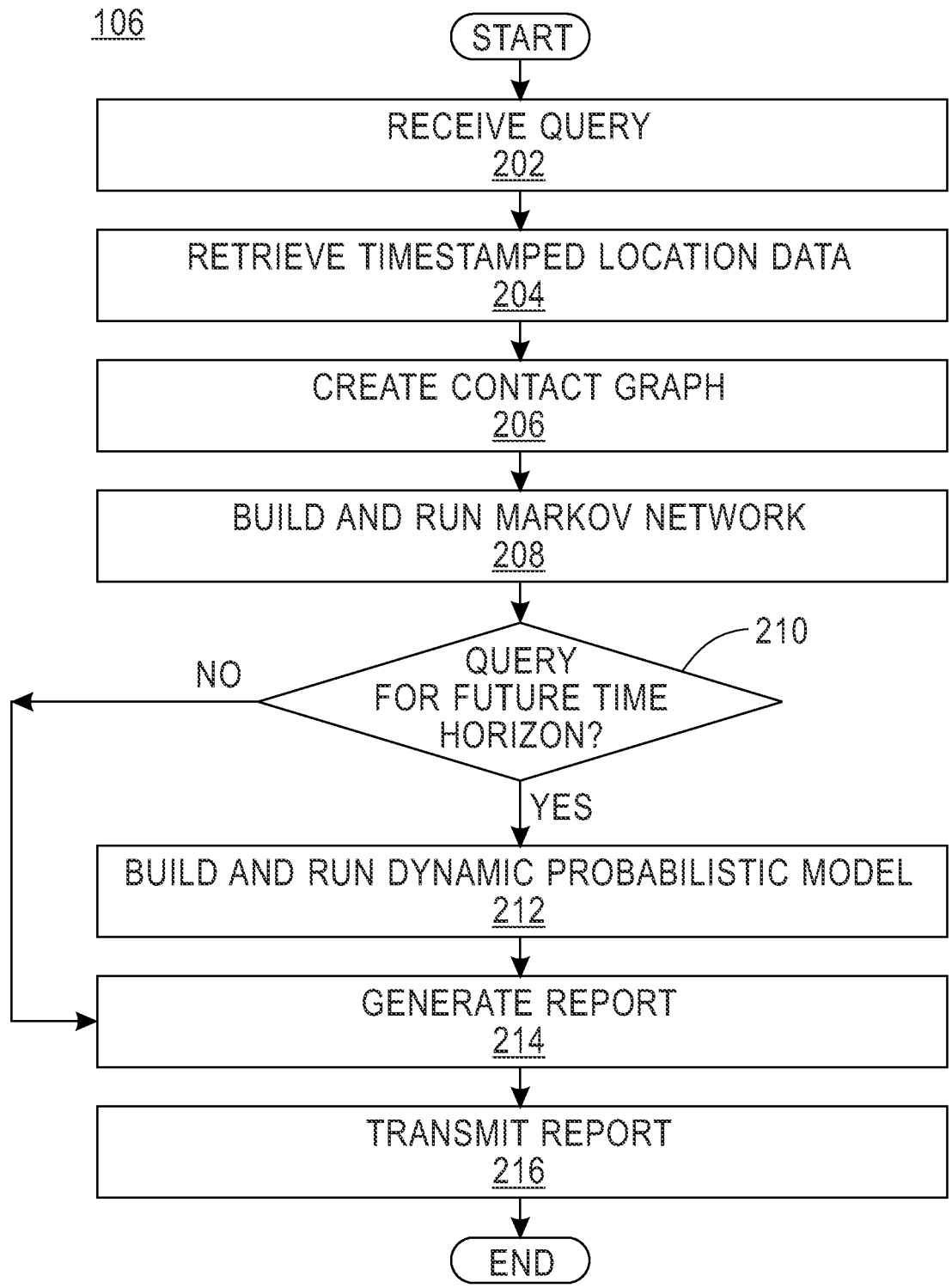
FIG. 2 is a flowchart depicting operational steps of a contact tracing engine, on a server computer within the distributed data processing environment of FIG. 1, for contact tracing during a pandemic, in accordance with an embodiment of the present invention.

FIG. 2 is a flowchart depicting operational steps of contact tracing engine 106, on server computer 104 within distributed data processing environment 100 of FIG. 1, for contact tracing during a pandemic, in accordance with an embodiment of the present invention.

Contact tracing engine 106 receives a query (step 202). In an embodiment, when a user of client computing device 114 requests contact tracing information, via contact tracing user interface 116, contact tracing engine 106 receives the query. For example, a user of client computing device 114 may request contact tracing information for a specific person, X, over a specific time period, such as over the last 14 days. The query may include a time period in the past, such as over the last 14 days, and/or the query may include a time horizon in the future.

Contact tracing engine 106 retrieves timestamped location data (step 204). In an embodiment, contact tracing engine 106 retrieves timestamped location data associated with person X over a period of time from one or more of GPS database 108 and credit card database 110. For example, contact tracing engine 106 may retrieve GPS data associated with a device of person X over a period of 14 days from GPS database 108, which shows the location of person X over that time period. In another example, contact tracing engine 106 may retrieve credit card transaction data associated with person X over the last 14 days from credit card database 110. Credit card transaction data may reveal the location of person X when person X used the credit card to make a purchase in the past 14 days.

Contact tracing engine 106 creates a contact graph (step 206). A contact graph displays one or more people that person X was in contact with over the specified period of time. In an embodiment, to create the contact graph, contact tracing engine 106 uses the retrieved timestamped location data associated with person X and determines one or more other people that were in the same location at the same time as person X to determine a pool of people associated with the timestamped locations of person X. In an embodiment, contact tracing engine 106 retrieves timestamped location data associated with the other people from one or more of GPS database 108 and credit card database 110. In another embodiment, the user of client computing device 114 requests data for the pool of users from a third party. For example, the user of client computing device 114 may request GPS data from a cell phone provider for users in a particular area over a period of time. Contact tracing engine 106 starts with person X and recursively traces the location of each other person in the pool. Contact tracing engine 106 determines whether a second person, A, is associated with a location within a pre-defined threshold distance of person X at a particular time. If contact tracing engine 106 determines that person A is within the pre-defined threshold distance of person X, then contact tracing engine 106 adds person A to the contact graph. For example, the pre-defined threshold distance may be six feet. In one embodiment, contact tracing engine 106 also determines if the period of time in which person X and person A were in the same location is greater than a pre-defined threshold period of time. For example, the pre-defined threshold period of time may be 15 minutes, such that if person X and person A are in the same location for more than 15 minutes, then contact tracing engine 106 adds person A to the contact graph. Once contact tracing engine 106 adds person A to the contact graph, contact tracing engine 106 proceeds in a similar manner to determine people who were in contact with person A over the same time period. Contact tracing engine 106 continues evaluating the timestamped location data of each other person in the pool until contact tracing engine 106 has evaluated every person in the pool and no more changes to the contact graph are possible. In an embodiment, contact tracing engine 106 limits the size of the contact graph. For example, contact tracing engine 106 may bound the contact graph to 25 people in the pool. An example of a contact graph is displayed and discussed in further detail with respect to FIG. 3A.

Contact tracing engine 106 builds and runs a Markov network (step 208). As would be recognized by a person of skill in the art, a Markov network is a graphical probabilistic model that can capture dependencies between person X and other people that may have been in contact with person X over a defined period of time. The Markov network models a joint probability distribution over person X and contacts of person X and captures the likelihood that a contact may have been infected by person X over the time period. In an embodiment, contact tracing engine 106 uses the contact graph to construct a Markov network with the same structure, i.e., nodes correspond to people and edges represent contact between the people. An example of a Markov network is displayed and discussed in further detail with respect to FIG. 3C.

In an embodiment, contact tracing engine 106 incorporates medical data corresponding to person X and the other people in the contact graph into the Markov network. The medical data includes any testing and associated results for the infection in question confirmed in the time period. In an embodiment, contact tracing engine 106 assigns a probability of infection. In an embodiment, the probability of infection is determined by a statistical analysis based on infection data for a population, based on scientific analysis, infection test results, and the like, and is outside the scope of the present invention. For example, on day 12 of the 14 day period, the retrieved GPS data indicates that person X and person A were within six feet of each other, and on that day the medical data indicates that person A has tested positive, i.e., is infected, thus, contact tracing engine 106 assigns a probability of 0.7 that person X will be infected on that day. In an embodiment, contact tracing engine 106 tabulates the medical data for each person in the model for each unit of time in the time period. An example of the tabulated data is displayed and discussed in further detail with respect to FIG. 3B.

In an embodiment, contact tracing engine 106 uses one or more of a plurality of algorithms to estimate a probability distribution from the data. For example, contact tracing engine 106 may use an expectation maximization algorithm. By using the algorithm, contact tracing engine 106 learns unary potentials, i.e., f(X), the prior likelihood that person X is infected. In addition, contact tracing engine 106 learns pairwise potentials, i.e., f(X, A), modeling the interaction between two people, or the potential/probability of person A being infected as a function of person X being infected. For example, if both person X and person A are infected, then the Markov network predicts that f(X, A) has a large value. If neither person X nor person A are infected, then the Markov network predicts that f(X, A) is a small value. Finally, if either one of person X or person A are infected, then the Markov network predicts that f(X, A) has a moderate value. In an embodiment, contact tracing engine 106 runs the Markov network model to generate data in response to the query.

Contact tracing engine 106 determines whether the query included a future time horizon (decision block 210). In an embodiment, the received query can request contact tracing engine 106 to predict a likelihood, or probability, that person X will be infected at a time in the future, e.g., tomorrow, based on historical data, i.e., the data in the Markov network.

If contact tracing engine 106 determines the query included a future time horizon ("yes" branch, decision block 210), then contact tracing engine 106 builds and runs a dynamic probabilistic model (step 212). In an embodiment, contact tracing engine 106 builds a dynamic probabilistic model that unfolds the Markov network over time to predict the likelihood of future infections for contacts of person X. In an embodiment, contact tracing engine 106 uses the Markov network to capture dependencies within a time slice of the future time horizon. For example, if the future time horizon is 14 days, then the time slice may be one day in the 14 days. For each contact of person X in the Markov network, contact tracing engine 106 learns a transition probability distribution. In an embodiment, contact tracing engine 106 uses one or more of a plurality of algorithms to estimate the transition probability distribution from the data. For example, contact tracing engine 106 may use an expectation maximization algorithm. Contact tracing engine 106 learns the distribution from the current time slice to the next time slice, creating a Markov network for each time slice. Contact tracing engine 106 returns a dynamic probabilistic model by "stitching together" the Markov networks for each time slice over the future time horizon. In an embodiment, contact tracing engine 106 runs the dynamic probabilistic model to generate data in response to the query. In an embodiment, contact tracing engine 106 runs a probabilistic inference to compute a marginal distribution of the probability that person A, for example, will be infected as a function of person X being infected. In an embodiment, contact tracing engine 106 uses one or more standard variable elimination algorithms to perform the computation.

Responsive to building and running the dynamic probabilistic model or if contact tracing engine 106 determines the query did not include a future time horizon ("no" branch, decision block 210), then contact tracing engine 106 generates a report (step 214). In an embodiment, based on the Markov network and/or the dynamic probabilistic model, contact tracing engine 106 generates one or more reports showing the likelihood of infection of one or more of the contacts of person X included in the contact graph. If the query included a future time horizon, then contact tracing engine 106 generates a report detailing the probability of each person to become infected over the time horizon using the dynamic probabilistic model. If the query did not include a future time horizon, then contact tracing engine 106 generates a report detailing the probability of each person in the contact graph to have already been infected.

Contact tracing engine 106 transmits the report (step 216). In an embodiment, contact tracing engine 106 transmits the one or more generated reports to the user of client computing device 114 via contact tracing user interface 116. For example, contact tracing engine 106 may transmit an email, a text message, a push notification, etc., to the user of client computing device 114 that includes the report in response to the query. In another example, contact tracing engine 106 may transmit a link to the one or more reports to the user of client computing device 114 via email, text message, push notification, etc., in response to the query. In an embodiment, contact tracing engine 106 transmits the report to a default list of government and/or health agencies.

FIG. 3A illustrates contact graph 302 of example 300 created by contact tracing engine 106, on server computer 104 within distributed data processing environment 100 of FIG. 1, in accordance with an embodiment of the present invention. Contact graph 302 is the contact graph for person X. In the example, contact graph 302 is bounded to a limit of eight people over a specified period of time. Person A, person B, and person C are direct contacts of person X, as depicted by the edges of the graph, i.e., the lines connecting person X to person A, person B, and person C. Direct contacts are those people that contact tracing engine 106 determined to be in the same location, i.e., within a threshold distance, and/or for a threshold period of time, at the same time as person X, based on the timestamped location data. Also depicted are indirect contacts of person X. Person D is a direct contact of both person A and person B, and therefore an indirect contact of person X. Person E is a direct contact of person B, and therefore an indirect contact of person X. Person F is a direct contact of person C, and therefore an indirect contact of person X. Person G is a direct contact of both person D and person E, and therefore an indirect contact of person X, as well as an indirect contact of person A, person B, and person C. The different shadings indicate the different dependencies between the people in the graph.

FIG. 3B illustrates tabulated medical data of example 300 used by the contact tracing engine 106 to build a Markov network model, on server computer 104 within distributed data processing environment 100 of FIG. 1, in accordance with an embodiment of the present invention. Table 304 includes a column for time intervals and columns for each person included in contact graph 302, to indicate whether or not each person was infected at each time interval. The time intervals may represent, for example, each day within a 14-day time period. Key 306 indicates that if a cell in table 304 depicts a "Y," then the person associated with the cell had a confirmed positive test for infection at that time interval, based on data that contact tracing engine 106 retrieved from medical database 112. Key 306 also indicates that if a cell in table 304 depicts an "N," then the person associated with the cell had a confirmed negative test for infection at that time interval, based on data that contact tracing engine 106 retrieved from medical database 112. An empty cell in table 304 indicates that no medical data is available for the associated person at that time interval.

FIG. 3C illustrates Markov network model 308 of example 300 built by contact tracing engine 106, on server computer 104 within distributed data processing environment 100 of FIG. 1, in accordance with an embodiment of the present invention. As depicted, Markov network model 308 has the same structure as contact graph 302. Although not visible in Markov network model 308, contact tracing engine 106 incorporated the medical data from table 304 into contact graph 302 to build Markov network model 308. Thus, as discussed with respect to step 208 of FIG. 2, using Markov network model 308, contact tracing engine 106 can determine a probability for both unary and pairwise infections for contacts of person X, based on person X being infected.

Figure 4:
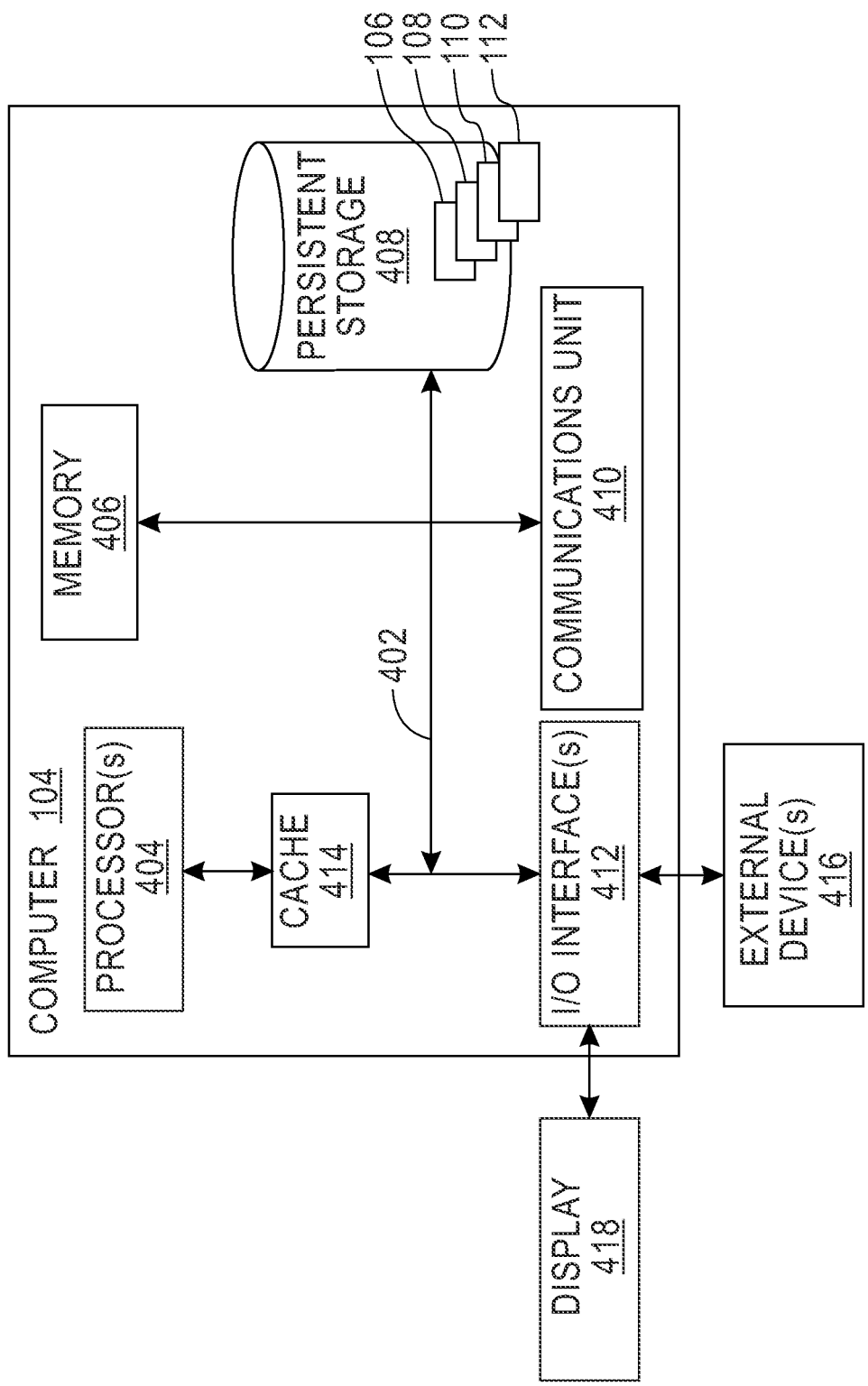
FIG. 4 depicts a block diagram of components of the server computer executing the contact tracing engine within the distributed data processing environment of FIG. 1, in accordance with an embodiment of the present invention.

FIG. 4 depicts a block diagram of components of server computer 104 within distributed data processing environment 100 of FIG. 1, in accordance with an embodiment of the present invention. It should be appreciated that FIG. 4 provides only an illustration of one implementation and does not imply any limitations with regard to the environments in which different embodiments can be implemented. Many modifications to the depicted environment can be made.

Server computer 104 can include processor(s) 404, cache 414, memory 406, persistent storage 408, communications unit 410, input/output (I/O) interface(s) 412 and communications fabric 402. Communications fabric 402 provides communications between cache 414, memory 406, persistent storage 408, communications unit 410, and input/output (I/O) interface(s) 412. Communications fabric 402 can be implemented with any architecture designed for passing data and/or control information between processors (such as microprocessors, communications and network processors, etc.), system memory, peripheral devices, and any other hardware components within a system. For example, communications fabric 402 can be implemented with one or more buses.

Memory 406 and persistent storage 408 are computer readable storage media. In this embodiment, memory 406 includes random access memory (RAM). In general, memory 406 can include any suitable volatile or non-volatile computer readable storage media. Cache 414 is a fast memory that enhances the performance of processor(s) 404 by holding recently accessed data, and data near recently accessed data, from memory 406.

Program instructions and data used to practice embodiments of the present invention, e.g., contact tracing engine 106, GPS database 108, credit card database 110, and medical database 112, are stored in persistent storage 408 for execution and/or access by one or more of the respective processor(s) 404 of server computer 104 via cache 414. In this embodiment, persistent storage 408 includes a magnetic hard disk drive. Alternatively, or in addition to a magnetic hard disk drive, persistent storage 408 can include a solid-state hard drive, a semiconductor storage device, a read-only memory (ROM), an erasable programmable read-only memory (EPROM), a flash memory, or any other computer readable storage media that is capable of storing program instructions or digital information.

The media used by persistent storage 408 may also be removable. For example, a removable hard drive may be used for persistent storage 408. Other examples include optical and magnetic disks, thumb drives, and smart cards that are inserted into a drive for transfer onto another computer readable storage medium that is also part of persistent storage 408.

Communications unit 410, in these examples, provides for communications with other data processing systems or devices, including resources of client computing device 114. In these examples, communications unit 410 includes one or more network interface cards. Communications unit 410 may provide communications through the use of either or both physical and wireless communications links. Contact tracing engine 106, GPS database 108, credit card database 110, medical database 112, and other programs and data used for implementation of the present invention, may be downloaded to persistent storage 408 of server computer 104 through communications unit 410.

I/O interface(s) 412 allows for input and output of data with other devices that may be connected to server computer 104. For example, I/O interface(s) 412 may provide a connection to external device(s) 416 such as a keyboard, a keypad, a touch screen, a microphone, a digital camera, and/or some other suitable input device. External device(s) 416 can also include portable computer readable storage media such as, for example, thumb drives, portable optical or magnetic disks, and memory cards. Software and data used to practice embodiments of the present invention, e.g., contact tracing engine 106, GPS database 108, credit card database 110, and medical database 112 on server computer 104, can be stored on such portable computer readable storage media and can be loaded onto persistent storage 408 via I/O interface(s) 412. I/O interface(s) 412 also connect to display 418.

Display 418 provides a mechanism to display data to a user and may be, for example, a computer monitor. Display 418 can also function as a touch screen, such as a display of a tablet computer.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product. The computer program product may include a computer readable storage medium (or media) having computer readable program instructions thereon for causing a processor to carry out aspects of the present invention.

The computer readable storage medium can be any tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, a special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, a segment, or a portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The foregoing descriptions of the various embodiments of the present invention have been presented for purposes of illustration and example, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A computer-implemented method comprising:
    receiving, by one or more computer processors, a query associated with contact tracing of a person with an infection, wherein the query included a future time horizon;
    retrieving, by one or more computer processors, timestamped location data associated with the person over a period of time;
    based on the retrieved timestamped location data, creating, by one or more computer processors, a contact graph associated with the person;

retrieving, by one or more computer processors, medical data associated with the person and the one or more other people that were in contact with the person over the period of time;

based on the contact graph and on the retrieved medical data, building, by one or more processors, a probabilistic model;

dividing, by one or more computer processors, the future time horizon into a set of equal subsets;

capturing, by one or more computer processors, one or more dependencies between the person and the one or more other people depicted in the contact graph within each subset of the set of equal subsets of the future time horizon using the probabilistic model;

based on a learned transition probability distribution for each of the one or more other people depicted in the contact graph for each subset of the set of subsets of the future time horizon, creating, by one or more computer processors, a unique graphical probabilistic model for each subset of the set of subsets of the future time horizon;

building, by one or more computer processors, a dynamic probabilistic model by stitching together the unique graphical probabilistic models for each subset of the set of subsets of the future time horizon for each of the one or more other people depicted in the contact graph; and running, by one or more computer processors, the dynamic probabilistic model to provide the prediction of the probability of infection of the one or more other people over the future time horizon.

2. The computer-implemented method of claim 1, wherein the probabilistic model is a Markov network.

3. The computer-implemented method of claim 1, further comprising:

based on the prediction of the probability of infection of the one or more other people over the period of time, generating, by one or more computer processors, a report; and transmitting, by one or more computer processors, the report.

4. The computer-implemented method of claim 1, further comprising:

learning, by one or more computer processors, the transition probability distribution for each of the one or more other people depicted in the contact graph for each subset of the set of subsets of the future time horizon.

5. The computer-implemented method of claim 1, wherein the timestamped location data includes global positioning system (GPS) data and credit card transaction data.

6. The computer-implemented method of claim 1, wherein creating the contact graph further comprises:

determining, by one or more computer processors, the person is within a pre-defined threshold distance of the one or more other people; and determining, by one or more computer processors, a period of time when the person was within the pre-defined threshold distance of the one or more other people is greater than a pre-defined threshold period of time.

7. The computer-implemented method of claim 1, wherein the medical data includes testing and associated results for the infection confirmed in the period of time.

8. A computer program product comprising:

one or more computer readable storage media and program instructions collectively stored on the one or more computer readable storage media, the stored program instructions comprising:

program instructions to receive a query associated with contact tracing of a person with an infection, wherein the query included a future time horizon;

program instructions to retrieve timestamped location data associated with the person over a period of time;

based on the retrieved timestamped location data, program instructions to create a contact graph associated with the person;

program instructions to retrieve medical data associated with the person and the one or more other people that were in contact with the person over the period of time;

based on the contact graph and on the retrieved medical data, program instructions to build a probabilistic model;

program instructions to divide the future time horizon into a set of equal subsets;

program instructions to capture one or more dependencies between the person and the one or more other people depicted in the contact graph within each subset of the set of equal subsets of the future time horizon using the probabilistic model;

based on a learned transition probability distribution for each of the one or more other people depicted in the contact graph for each subset of the set of subsets of the future time horizon, program instructions to create a unique graphical probabilistic model for each subset of the set of subsets of the future time horizon;

program instructions to build a dynamic probabilistic model by stitching together the unique graphical probabilistic models for each subset of the set of subsets of the future time horizon for each of the one or more other people depicted in the contact graph; and program instructions to run the dynamic probabilistic model to provide the prediction of the probability of infection of the one or more other people over the future time horizon.

9. The computer program product of claim 8, wherein the probabilistic model is a Markov network.

10. The computer program product of claim 8, the stored program instructions further comprising:

based on the prediction of the probability of infection of the one or more other people over the period of time, program instructions to generate a report; and program instructions to transmit the report.

11. The computer program product of claim 8, the stored program instructions further comprising:

program instructions to learn the transition probability distribution for each of the one or more other people depicted in the contact graph for each subset of the set of subsets of the future time horizon.

12. The computer program product of claim 8, wherein the timestamped location data includes global positioning system (GPS) data and credit card transaction data.

13. The computer program product of claim 8, wherein the program instructions to create the contact graph comprise:

program instructions to determine the person is within a pre-defined threshold distance of the one or more other people; and program instructions to determine a period of time when the person was within the pre-defined threshold distance of the one or more other people is greater than a pre-defined threshold period of time.

14. The computer program product of claim 8, wherein the medical data includes testing and associated results for the infection confirmed in the period of time.

15. A computer system comprising:
one or more computer processors;
one or more computer readable storage media;
program instructions collectively stored on the one or more computer readable storage media for execution by at least one of the one or more computer processors, the stored program instructions comprising:
program instructions to receive a query associated with contact tracing of a person with an infection, wherein the query included a future time horizon;
program instructions to retrieve timestamped location data associated with the person over a period of time;
based on the retrieved timestamped location data, program instructions to create a contact graph associated with the person;
program instructions to retrieve medical data associated with the person and the one or more other people that were in contact with the person over the period of time;
based on the contact graph and on the retrieved medical data, program instructions to build a probabilistic model; and
program instructions to divide the future time horizon into a set of equal subsets;
program instructions to capture one or more dependencies between the person and the one or more other people depicted in the contact graph within each subset of the set of equal subsets of the future time horizon using the probabilistic model;
based on a learned transition probability distribution for each of the one or more other people depicted in the contact graph for each subset of the set of subsets of the future time horizon, program instructions to create a unique graphical probabilistic model for each subset of the set of subsets of the future time horizon;
program instructions to build a dynamic probabilistic model by stitching together the unique graphical probabilistic models for each subset of the set of subsets of the future time horizon for each of the one or more other people depicted in the contact graph; and
program instructions to run the dynamic probabilistic model to provide the prediction of the probability of infection of the one or more other people over the future time horizon.

16. The computer system of claim 15, wherein the probabilistic model is a Markov network.

17. The computer system of claim 15, the stored program instructions further comprising:
based on the prediction of the probability of infection of the one or more other people over the period of time, program instructions to generate a report; and
program instructions to transmit the report.

18. The computer system of claim 15, the stored program instructions further comprising:
program instructions to learn the transition probability distribution for each of the one or more other people depicted in the contact graph for each subset of the set of subsets of the future time horizon.

19. The computer system of claim 15, wherein the timestamped location data includes global positioning system (GPS) data and credit card transaction data.

20. The computer system of claim 15, wherein the program instructions to create the contact graph comprise:
program instructions to determine the person is within a pre-defined threshold distance of the one or more other people; and
program instructions to determine a period of time when the person was within the pre-defined threshold distance of the one or more other people is greater than a pre-defined threshold period of time.

* * * * *